US007199257B1

(12) United States Patent
Sörös et al.

(10) Patent No.: US 7,199,257 B1
(45) Date of Patent: Apr. 3, 2007

(54) PROCESS FOR THE SYNTHESIS OF N-(4-CYANO-3-TRIFLUOROMETHYLPHE-NYL)-3-(4-FLUOROPHENYLSULFONYL)-2-HYDROXY-2-METHYLPROPIONAMIDE

(75) Inventors: Bela Sörös, Budapest (HU); Zoltan Tuba, Budapest (HU); György Galik, Budapest (HU); Adam Bor, Budaörs (HU); Adam Demeter, Budapest (HU); Ferenc Trischler, Budapest (HU); Janos Horvath, Bölcske (HU); Janos Brlik, Budapest (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 0 days.

(21) Appl. No.: 10/030,665

(22) PCT Filed: May 26, 2000

(86) PCT No.: PCT/HU00/00049

§ 371 (c)(1),
(2), (4) Date: Nov. 30, 2001

(87) PCT Pub. No.: WO01/00608

PCT Pub. Date: Jan. 4, 2001

(30) Foreign Application Priority Data

Jun. 10, 1999 (HU) .................................. 9901937

(51) Int. Cl.
*C07C 255/50* (2006.01)
(52) U.S. Cl. ...................................... 558/413; 558/414
(58) Field of Classification Search ................ 558/303, 558/411, 413, 414
See application file for complete search history.

(56) References Cited

U.S. PATENT DOCUMENTS 6,740,770 B2 * 5/2004 Shintaku et al. ............ 558/413

6,818,766 B2 * 11/2004 Thijs et al. ................. 544/105

FOREIGN PATENT DOCUMENTS

| EP | 0 100 172 | 2/1984 |
| HU | 191296 B | 7/1982 |
| WO | WO 95/19770 | 7/1995 |
| WO | WO 98/55153 | 12/1998 |

OTHER PUBLICATIONS

Nonsteroidal Antiandrogen, Synthesis & Structure . . . By Tucker et al. (J.Med. Chem. 1988, 31).
Resolution of the Nonsteroidal Antiandrogen . . . by Tucketr et al. (J. Med. Chem. 1988, 31).
J. Med. Chem. 1986, 29, 2184-2190; Winston Ho et al; Alkylglycidic Acids: Potential new hypoglycemic agents.
J. Med. Chem. 1988, 31, 954-959; Howard Tucker et al; Nonsteroidal Antiandrogens. Synthesis and structure . . . .
J. Med. Chem. 1988, 31, 885-887; Howard Tucker et al; Resolution of the Nonsteroidal Antiandrogen 4'-Cyano . . . .
Epoxidation of Olefins; Jan. 5, 1955; vol. 77; pp. 89-92; William D. Emmons et al; Peroxytrifluoroacetic Acid. IV.
Vol. 81; pp. 680-683; Feb. 5, 1959; Donald L. MacPeek et al; Synthesis of Glycidic Esters by Epoxidation of . . . .
Proceedings of Asco; vol. 15; Mar. 1996; 684; Mary Anne Fenton et al; Bicalutamide for androgen-independent . . . .
Zh. Org. Khim.; vol. 7; B.T. Hockoe; 1971; pp. 2221-2222.

* cited by examiner

*Primary Examiner*—Golam M. M. Shameem
(74) *Attorney, Agent, or Firm*—Jonathan Myers; Andrew Wilford

(57) ABSTRACT

A new process is disclosed for the synthesis of racemic or optically pure N-[4-cyano-3-trifluoro-methyl-phenyl]-3[4-fluorophenyl-sulfonyl]-2-hydroxy-2-methylpropionamide. The process includes the formation of several novel intermediates in the synthesis.

18 Claims, 6 Drawing Sheets (I)

(Ia)

(Ib)

Figure 1:
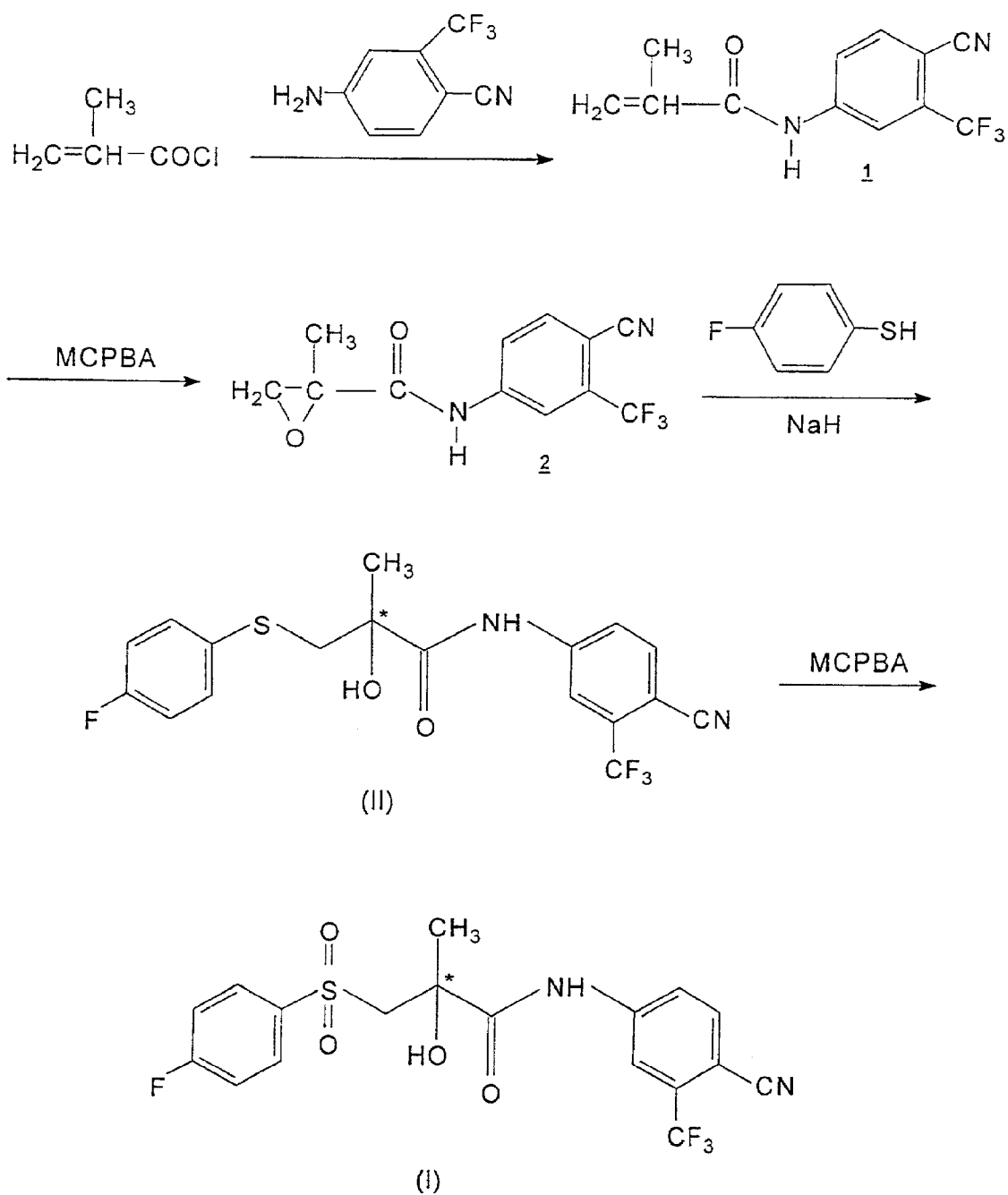
Figure 2:
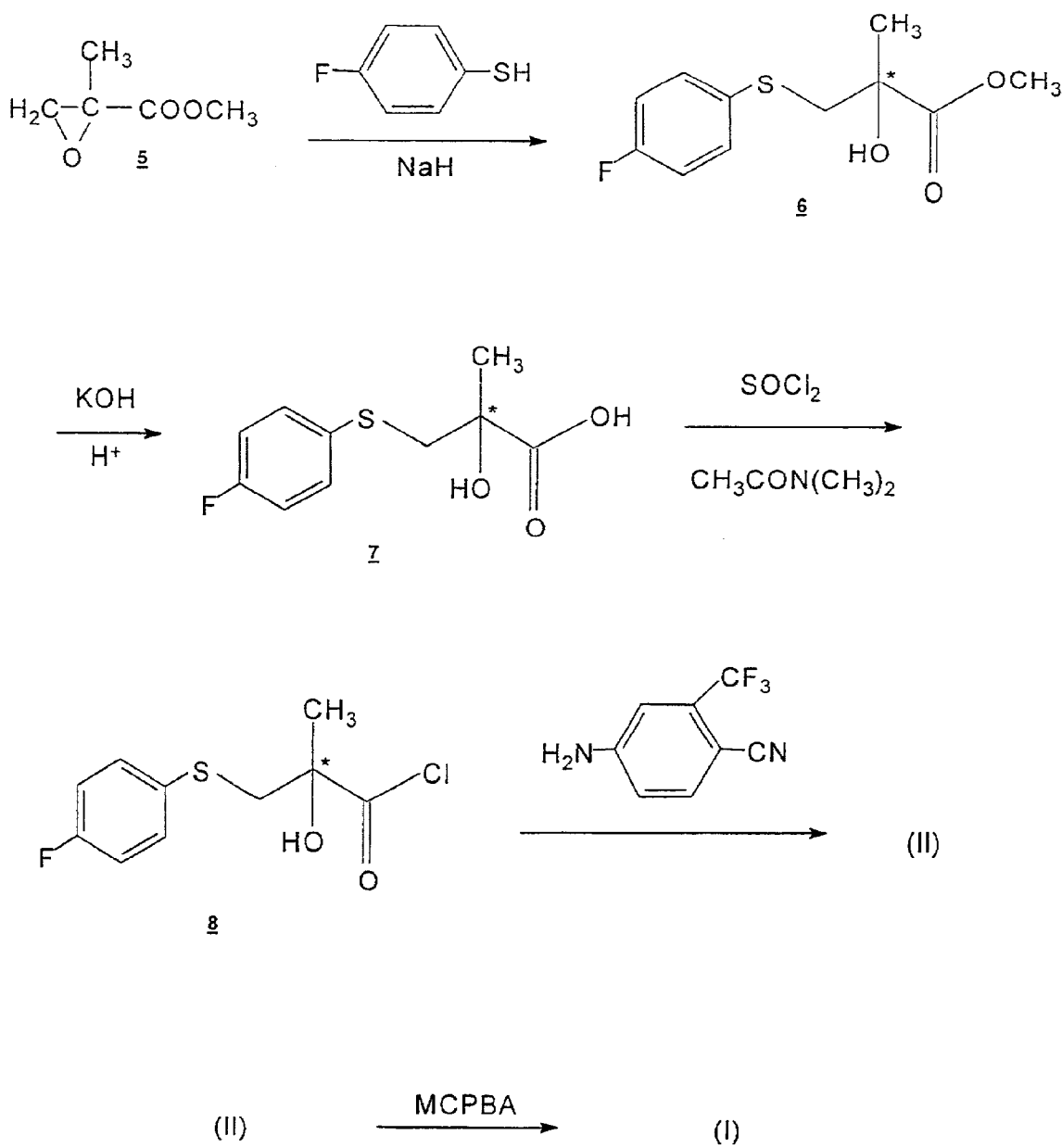

PROCESS FOR THE SYNTHESIS OF N-(4-CYANO-3-TRIFLUOROMETHYLPHENYL)-3-(4-FLUOROPHENYLSULFONYL)-2-HYDROXY-2-METHYLPROPIONAMIDE

CROSS REFERENCE TO RELATED APPLICATIONS

This application is a 371 of PCT/HU00/00049 filed 26 May 2000 claiming the priority of Hungarian Patent Application P9901937 filed 10 Jun. 1999.

FIELD OF THE INVENTION

The invention relates to a new process for the synthesis of the known racemic and optically pure R-(−)- and S-(+)-N-[4-cyano-3-trifluoromethyl-phenyl]-3-[4-fluorophenylsulfonyl]-2-hydroxy-2-methyl-propionamide of formula (I), (Ia) and (Ib), respectively.

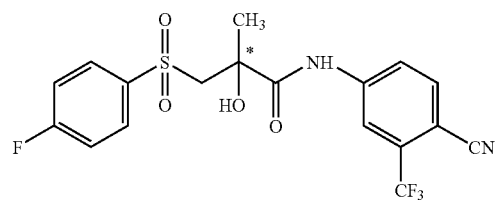
(I)

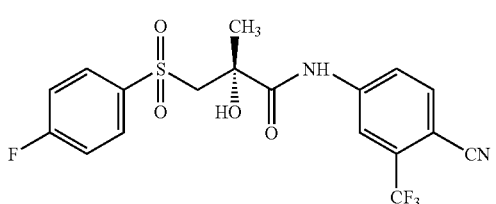
(Ia)

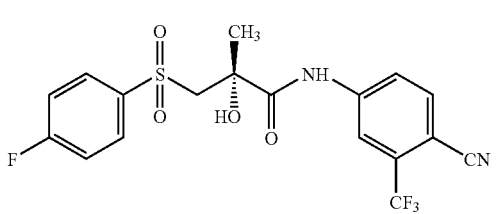
(Ib)

BACKGROUND OF THE INVENTION

N-[4-cyano-3-trifluoromethyl-phenyl]-3-[4-fluorophenylsulfonyl]-2-hydroxy-2-methyl-propionamide was known as Bicalutamide in therapy.

The racemic and the optically pure Bicalutamide have antiandrogen activity. They decrease the testosterone level selectively in the prostate without influencing the regulation mechanisms of the hypothalamus (the LH-level/testosterone-level negative feedback mechanism). They have higher and more selective biological and clinical activity as compared to Flutamide {2-methyl-N-[4-nitro-3-trifluoromethyl-phenyl]-propionamide}, since they do not increase the testosterone- and the LH-level even at 19 times concentration of $ED_{50}$ in the human body, while the Flutamide doubles them at 3.5 times concentration of $ED_{50}$ [J. Med. Chem., 31, 954–959 (1988)]. The effect of daily 50 and 150 mg dose was tested in the clinical practice [Proc. Am. Soc. Oncology, 15, 684 (1996)]. It has been found, that in the case of primary prostate tumors the racemic Bicalutamide combined with an LHRH analog was at least as active as castration, while in the case of secondary tumors it does not substitute that.

The international patent No. WO 95/19770 describes the use of the R-(−) enantiomer. From the two enantiomers the R-(−) isomer was more active. The authors claim, that treatment with the R-(−) isomer was more advantageous, on the one hand because less substance was needed and on the other hand the R-(−) enantiomer was peripherally antiandrogen and therefor its side-effects (headache, gynecomistia, giddiness) were less pronounced, than that of the racemate.

The synthesis of racemic and optically pure enantiomers of formula (I), (Ia) and (Ib), respectively, was described in the following literature:

The patent No. EP 100172 describes the synthesis of new acylanilides by different known methods. The description contains the synthesis of compounds of formula (I), (Ia) and (Ib), too. Some of the synthetic methods disclosed in EP 100172 are described in J. Med. Chem., 31. 954–959 (1988), too.

Method 1 from EP 100172

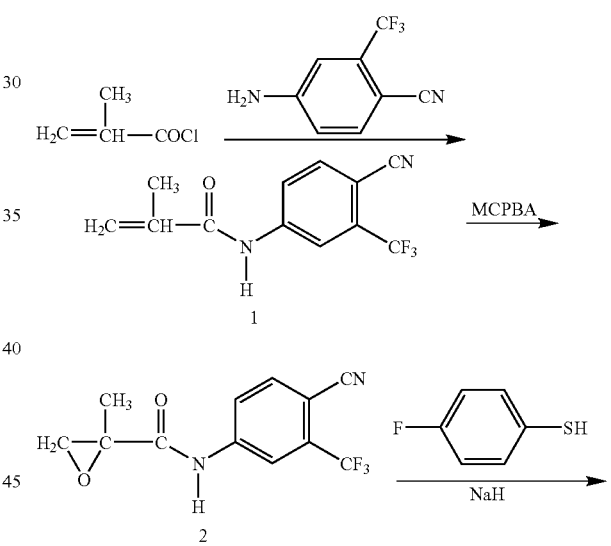

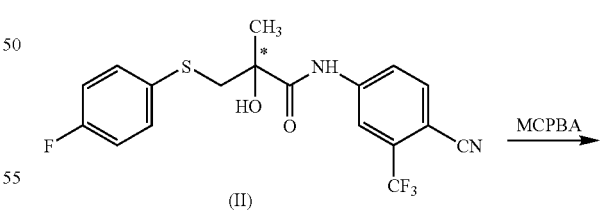
(II)

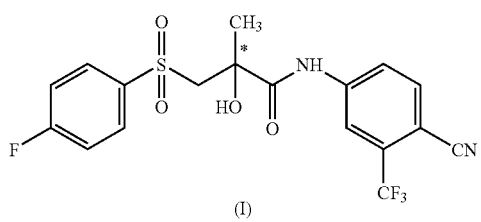
(I)

Method 2 from EP 100172

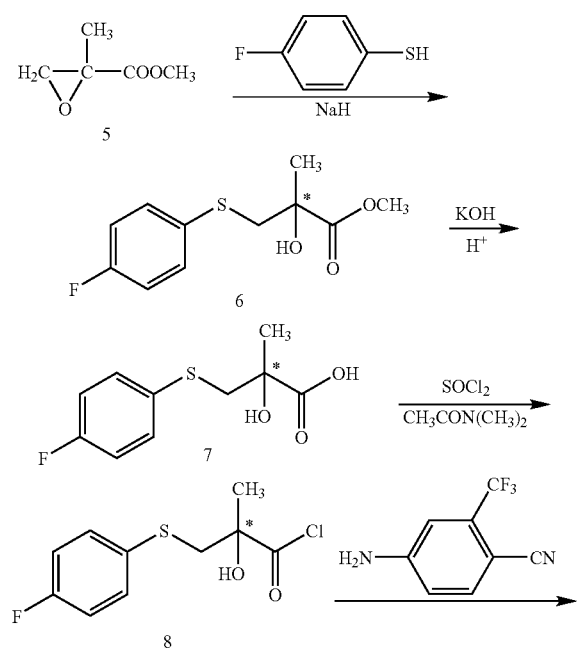

Method 3 from EP 100172

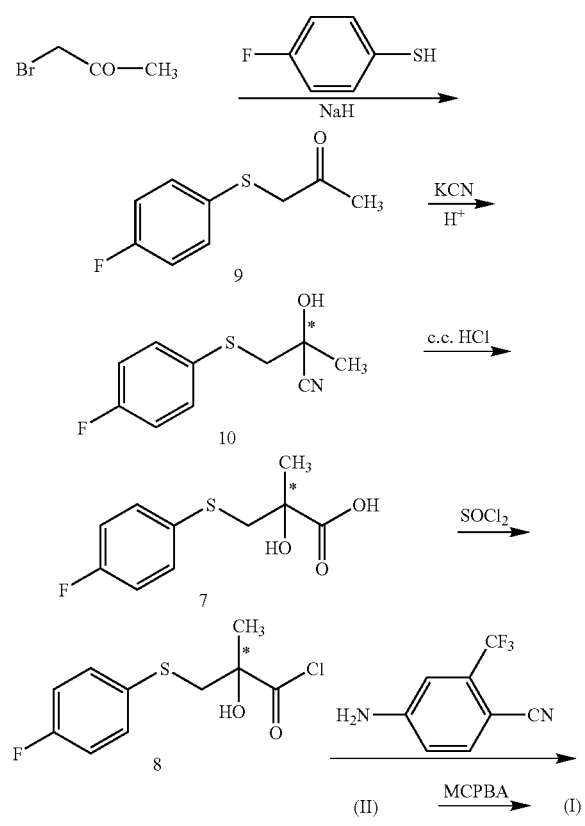

Method 4 Asymmetric Synthesis from J. Med. Chem., 31, B85 to 887 (1988)

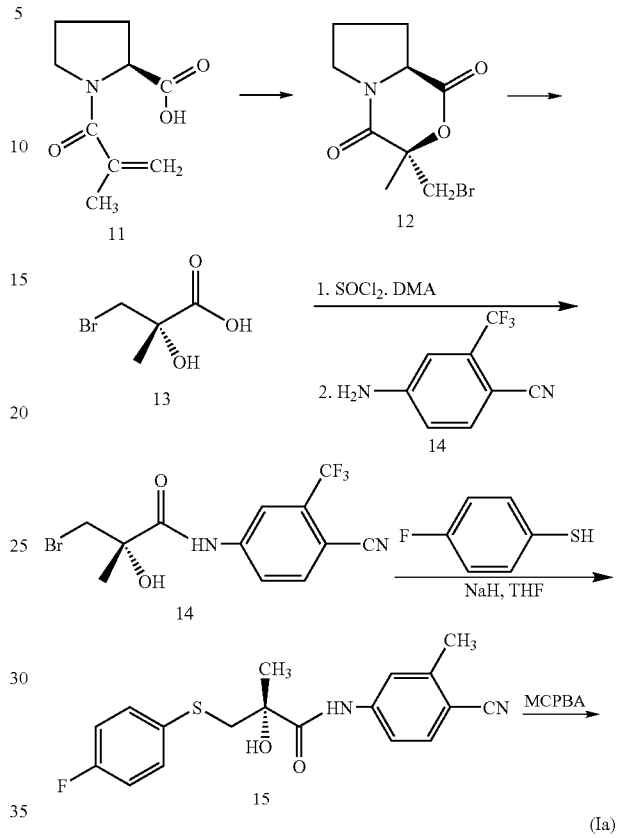

The separation of the antipodes was described in detail in J. Med. Chem., 31, 885–887 (1988), which was also described in the patent No. EP100172.

According to the first process disclosed in EP 100172 (Method 1 hereinabove) the starting methacryl acid chloride was reacted with 4-amino-2-trifluoromethyl-benzonitrile in dimethylacetamide at 5° C. and the so obtained anilide of formula (1) was refluxed with m-chloroperbenzoic acid (MCPBA) in 1,1,1-trichloroethane in the presence of 2,5-di-tert-butyl-methylphenol (this was highly explosive). After the completion of the epoxidation reaction the formed epoxide of formula (2) was isolated. The opening of the epoxide ring of compound of formula (2) was carried out with 4-fluorothiophenol in the presence of sodium hydride, then the obtained thioether derivative of formula (II) was oxidized by known method with m-chloroperbenzoic acid in dichloromethane to yield the final product of formula (I).

According to the second process disclosed in EP 100172 (Method 2 hereinabove) the starting material was methyl methacrylate, which can be converted into epoxide only under harsh conditions (i.e. with peracetic acid in ethyl acetate at 75° C. [J. Am. Chem., 81, 680 (1959)], or with 90% hydrogen peroxide—trifluoroacetic anhydride at 40° C. [J. Am. Chem., 77, 89 (1955)], or with MCPBA in dichloromethane at ° C. in low yield [J. Med. Chem., 29. 2184 (1986)]. The epoxidation under the above mentioned conditions can be explosive. The methyl 2-methyl-oxirane-carboxylate of formula (5), which was obtained by epoxidation, was reacted with 4-fluorothiophenol in the presence of sodium hydride. The obtained methyl 2-hydroxy-2-methyl-3-(4-fluorophenylthio)-propionate of formula (6) was hydrolyzed with potassium hydroxide in aqueous ethanol over a period of 22 h to yield the 2-hydroxy-2-methyl-3-(4-fluorophenylthio)-propionic acid of formula (7), which was converted into acid chloride of formula (8) with thionyl chloride in dimethyl acetamide at −15° C. The obtained acid chloride was reacted with 4-amino-2-trifluoromethyl-benzonitrile in dimethylacetamide at −15° C. to yield the thioether derivative of formula (II), which was given in the reaction scheme of Method 1. The oxidation of the thioether derivative was carried out according to the reaction scheme of Method 1.

Figure 3:
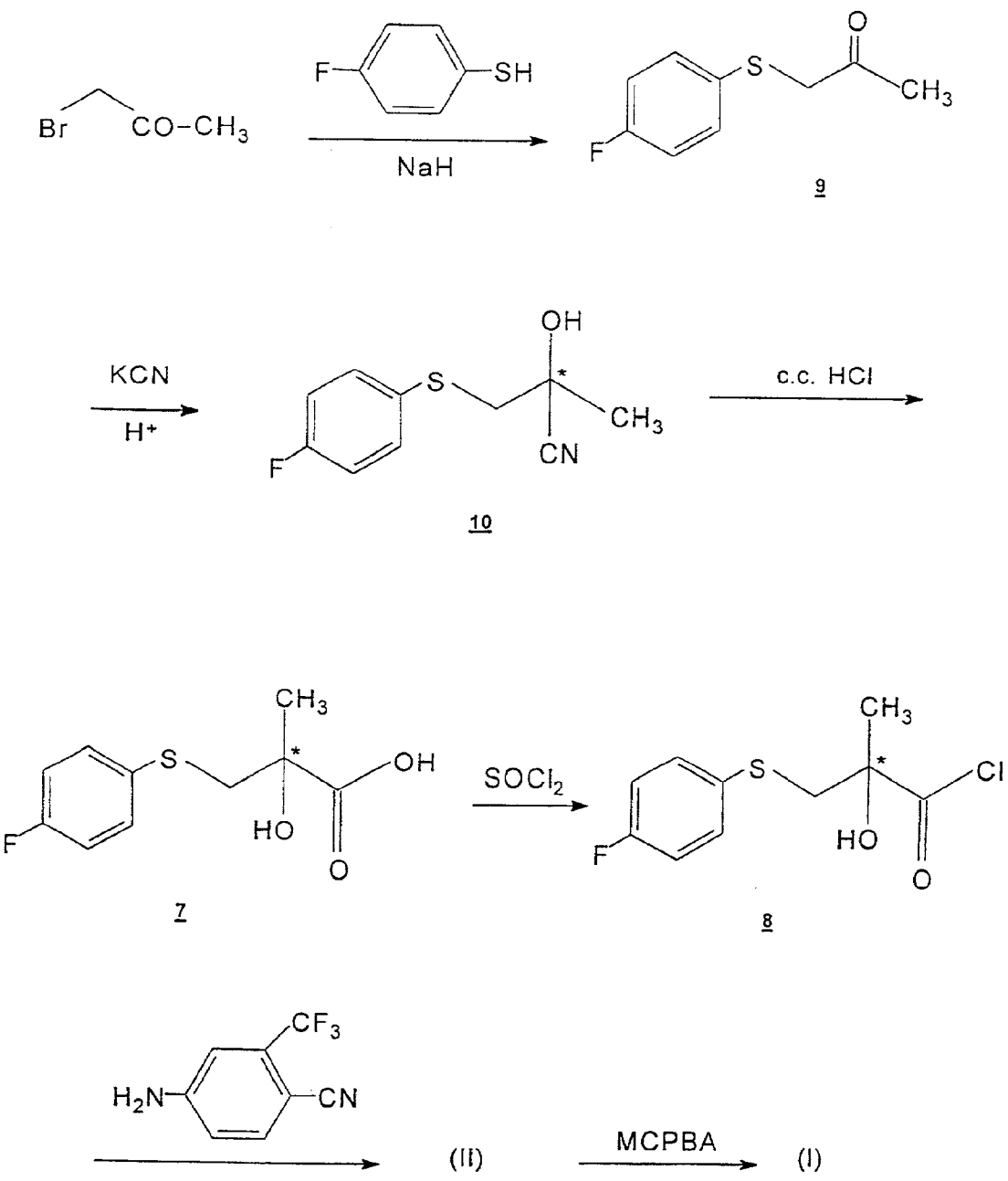

The starting material of the synthesis given on FIG. 3 was bromo-acetone, which was reacted according to the literature [Zh. Org. Khim., 7, 2221, (1871)] with 4-fluorothiophenol in the presence of triethylamine, the obtained thioether derivative of formula (9) was reacted with potassium cyanide under acidic conditions to yield the cyanohydrine derivative of formula (10). The 2-hydroxy-2-methyl-3-(4-fluorophenylthio)-propionic acid of formula (7) was obtained from the latter by acidic hydrolysis. The 2-hydroxy-2-methyl-3-(4-fluorophenylthio)-propionic acid of formula (7) was converted into acid chloride with thionyl chloride and the latter was transformed into amide and oxidized to yield (±)-Bicalutamide as given above.

Two procedures were known for the synthesis of the optically pure Bicalutamide:

According to one procedure [patent No. EP 100172 and J. Med. Chem., 31, 885–887 (1988)] the thioether derivative of formula (II), which was the key-intermediate of the synthesis of (±)-Bicalutamide, was synthesized, then the resolution was carried out by esterification of the hydroxyl group of the thioether derivative with optically pure R-(−)-camphoric acid chloride, the obtained diastereomers were separated by fractional crystallization or preferably by chromatography, then the optically pure esters were hydrolyzed to yield the corresponding alcohol derivatives and oxidized to give the optically pure Bicalutamide.

Figure 4:
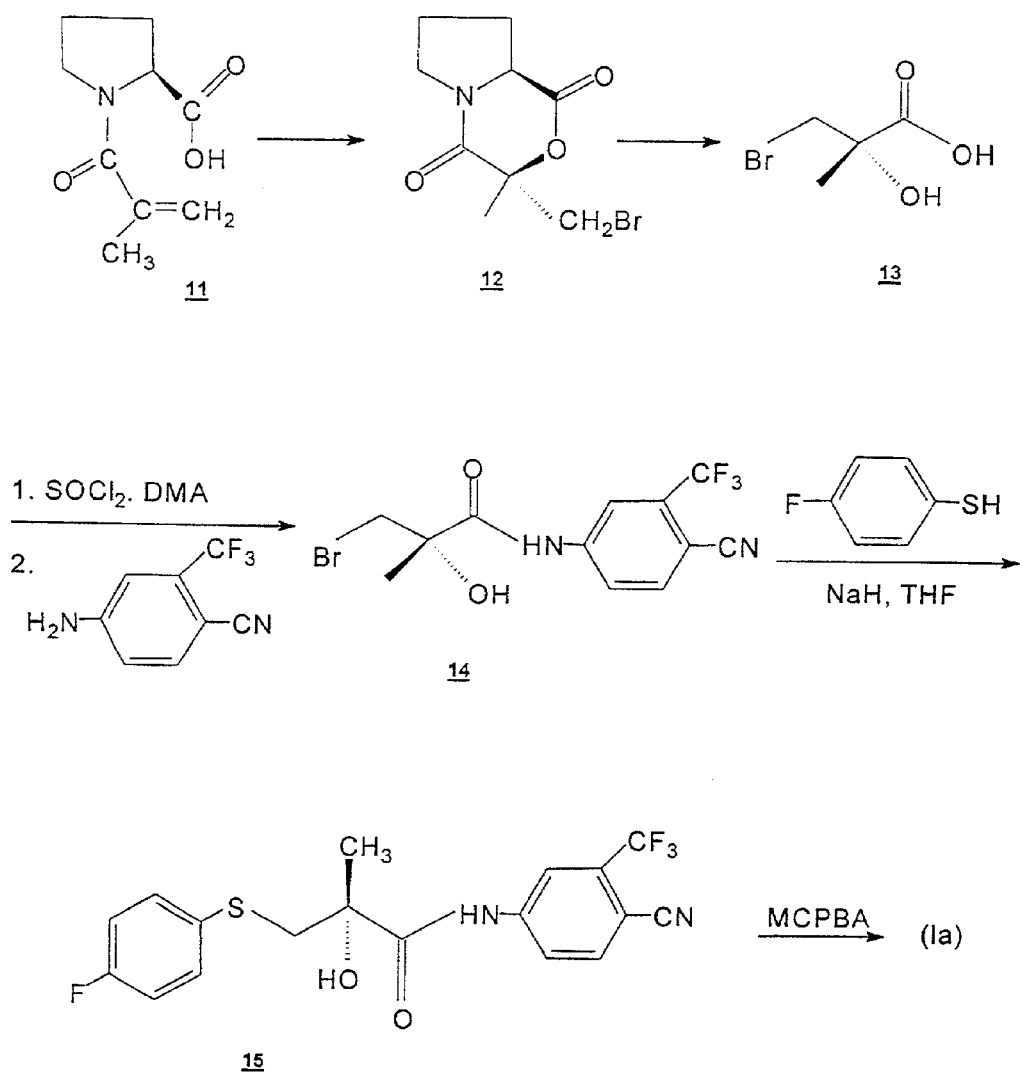
Figure 5:
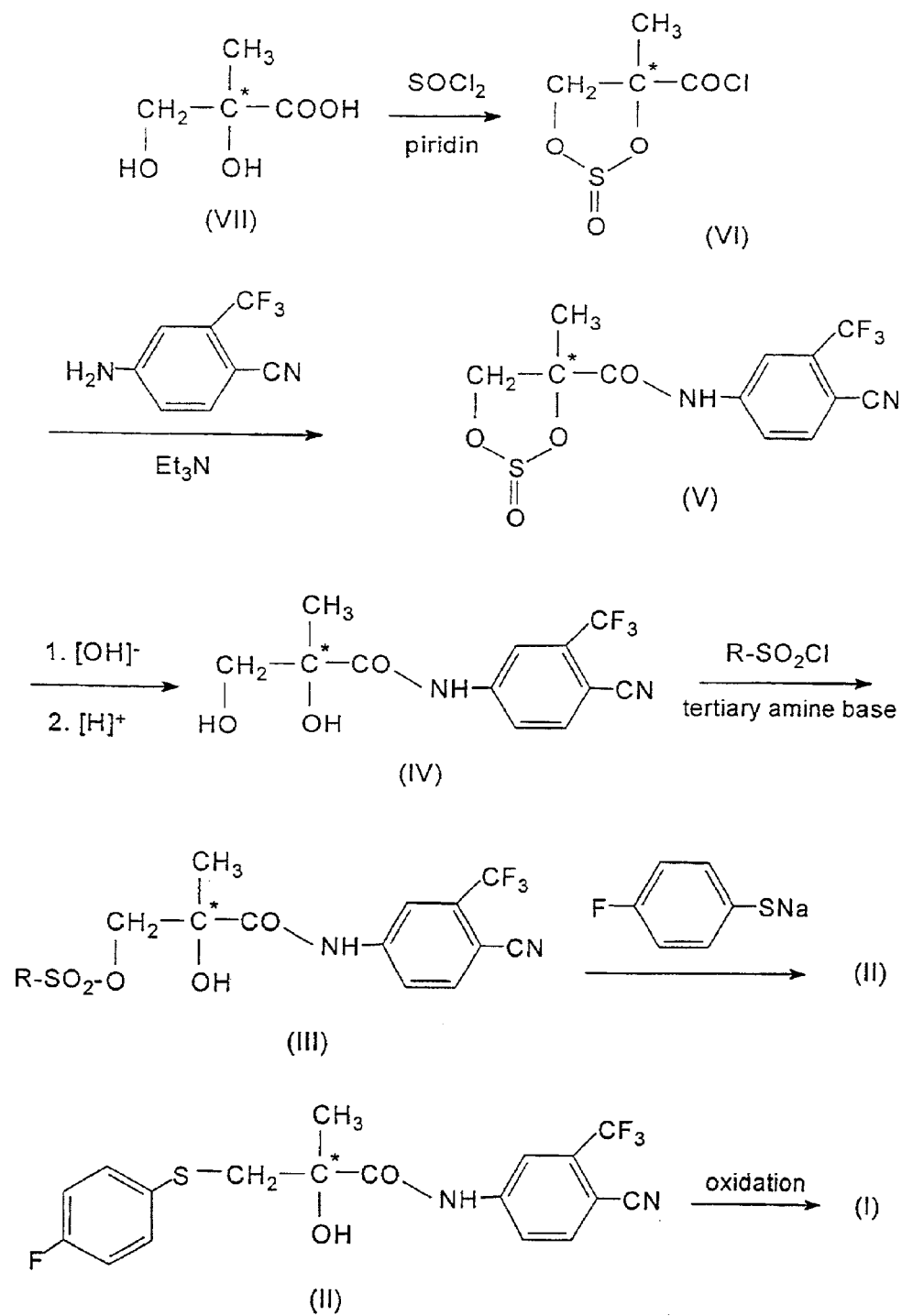
Figure 6:
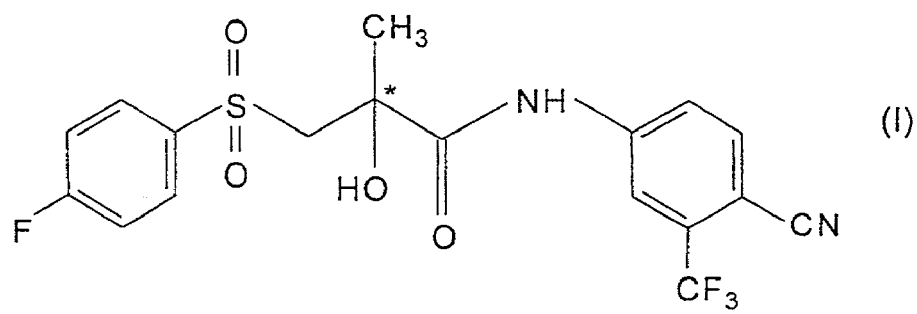
Figure 6:
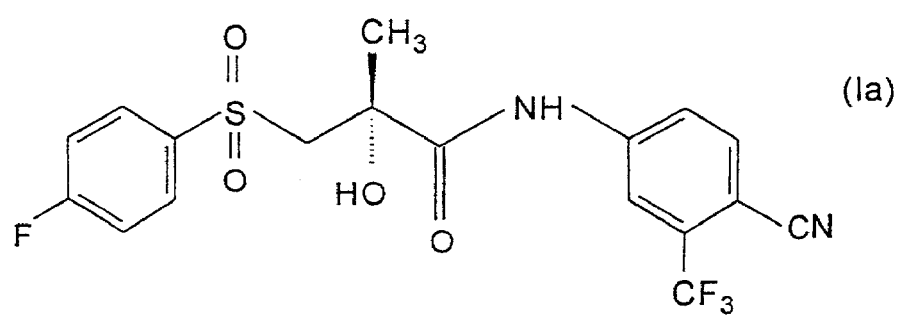
Figure 6:
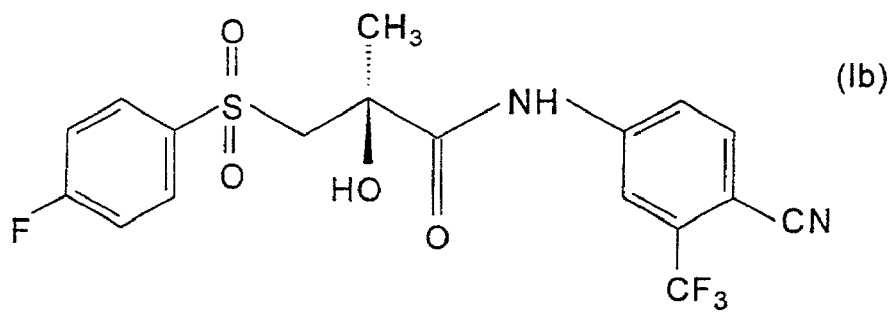

According to the other procedure [J. Med. Chem., 31, 885–887 (1988)], which was shown on FIG. 4, the optically pure S-(+)-Bicalutamide was obtained by asymmetric synthesis. The starting material of the synthesis was S-(+)-N-methacryloyl-proline of formula (11), which was reacted with N-bromo-succinimide in dimethyl formamide to yield the 3(S)-(bromomethyl)-3(S)-methyl-1,4-dioxo-3,4,6,7,8,8a (S)-hexahydro-1-H-pyrrolo[2,1-c][1,4]-oxazine of formula (12). The latter was hydrolyzed with hydrochloric acid to give the S-(+)-3-bromo-2-hydroxy-2-methyl-propionic acid of formula (13), which was converted into the corresponding acid chloride with thionyl chloride. The acid chloride was reacted with 4-amino-2-trifluoromethyl-benzonitrile to yield the S-(+)-N-{4-cyano-(3-trifluoromethyl)}-3-bromo-2-methyl-2-hydroxy-propionamide of formula (14). The latter was reacted with 4-fluorothiophenol in the presence of sodium hydride to give the (S)-(+)-N-[4-cyano-3-(trifluoromethyl)-phenyl]-3-[(4-fluorophenyl)-thio]-2-hydroxy-2-methyl-propionamide of formula (15), which was oxidized by known method with m-chloroperbenzoic acid to yield the optically pure S-(+)-Bicalutamide. The R-(−)-Bicalutamide can be synthesized the same way starting from R-(−)-N-methacryloyl-proline.

It was very important to examine a procedure from the point of industrial applicability, whether the procedure fulfils the following requirements:

1) The starting materials of the procedure should be easily available and as cheap as possible.

2) The use of harmful reagents should be avoided during the course of the procedure.

3) The synthesis should be safe from the point of environmental protection.

4) The formation of by-products and ballast materials, which cannot be used or processed further, should be minimized during the course of the procedure.

5) The reaction vessels generally used in pharmaceutical and chemical industry should be applicable for the realization of the synthesis.

6) It was very important, that the synthesis should give pure final product, which does not need further, expensive purification.

All of the syntheses described in the literature apply steps, which do not fulfil one or other of the above conditions.

According to Method 3 disclosed hereinabove the synthesis of cyanohydrine derivative of formula (10) and its further reaction under acidic conditions was dangerous for health. The hydrolysis of the cyanohydrine in the presence of concentrated hydrochloric acid at 110° C. or with hydrochloric acid in acetic acid requires special equipment. The use of sodium hydride in tetrahydrofuran was an inflammable step. In the second step (epoxidation) of the first procedure the oxidation was carried out with m-chloroperbenzoic acid. This oxidation step, which was carried out at high temperature (i.e. at 120° C.), was explosive.

The known procedures, which were carried out only on few-gram-scale, can lead to further, unexpected problems during the industrial realization. (i.e. an oxidation carried out in a few m³ reactor can easily 'run over', resulting in an explosion; weighing and adding a large quantity of sodium hydride needs special attention, etc.)

The modern requirements of pharmacopoeia specify numerous analyzing methods, i.e. thin layer or liquid chromatographic content determination, moreover fix and limit the number and the quantity of the impurities, therefor it was a basic requirement, that the product formed during the synthesis should contain the least impurities possible.

OBJECT OF THE INVENTION

Taking into consideration the above mentioned our aim was to elaborate a new, environmental protective, safe, industrially applicable process, which was devoid of the insufficiencies of the known procedures and makes possible the synthesis of both the racemic and the optically pure desired compounds in high yield and was easily realizable industrially.

SUMMARY OF THE INVENTION

Surprisingly it was found, that the following process fulfils the above requirements:

the racemic or optically pure 2.3-dihydroxy-2-methyl-propionic acid of formula (VII)

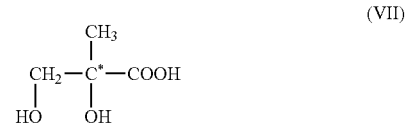

was reacted with thionyl chloride in a halogenated hydrocarbon or in an aromatic solvent in the presence of an aromatic amine as base, the obtained racemic or optically pure 4-chloro-carbonyl-4-methyl-1,3,2-dioxathiolane-2-one of formula (VI)

was reacted with 4-cyano-3-trifluoromethyl-aniline in an inert solvent in the presence of a tertiary amine as base between −40 and 0° C., the obtained racemic or optically pure 4-{[4-cyano-3-(trifluoromethyl)-anilino]-carbonyl}-4-methyl-1,3,2-dioxathiolane-2-one of formula (V)

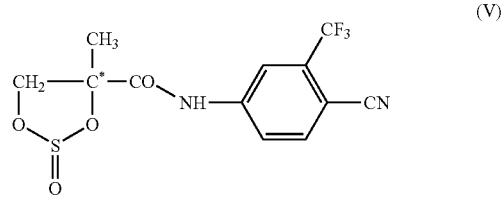

was hydrolyzed under aqueous basic conditions, the formed racemic or optically pure N-[4-cyano-3-(trifluoromethyl)-phenyl]-2,3-dihydroxy-2-methyl-propionamide of formula (IV)

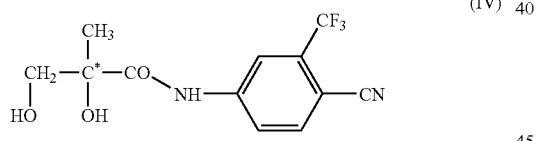

was sulfonylated with a sulfonyl halogenide of formula R—SO$_2$—X—wherein the meaning of R was methyl, p-tolyl or p-bromo-phenyl group and X represents a halogen atom—in a halogenated hydrocarbon as solvent in the presence of a tertiary amine as base, the obtained racemic or optically pure sulfonic ester derivative of formula (III)

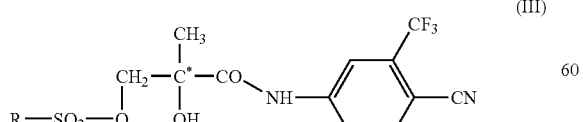

wherein R represents methyl, p-tolyl or p-bromo-phenyl group was reacted with 4-fluorothiophenol in the presence of a base, finally the obtained racemic or optically pure thioether derivative of formula (II)

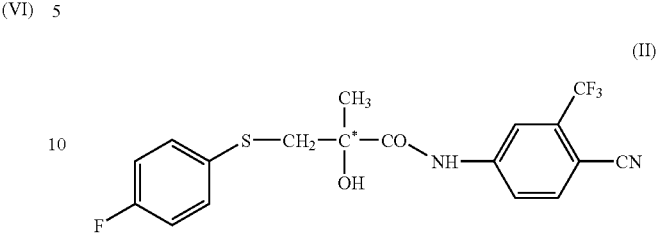

was oxidized i) with an inorganic peroxy salt in a mixture of water and a solvent miscible or not miscible with water, in the latter case in the presence of a phase transfer catalyst, or ii) with aqueous hydrogen peroxide a) in a $C_1$–$C_4$ aliphatic carboxylic acid, or b) under aqueous basic conditions, in given case in the presence of an organic solvent miscible with water, or c) in an organic solvent not miscible with water in the presence of a phase transfer catalyst and a salt of a metal belonging to the vanadium or chromium group.

The process according to our invention is illustrated below, the individual reaction steps were preferably carried out the following way:

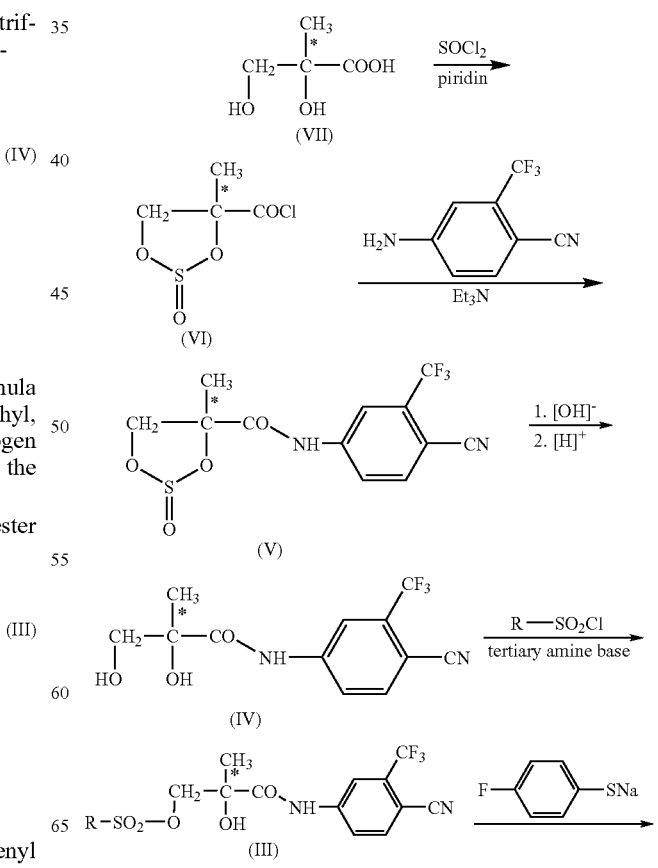

-continued

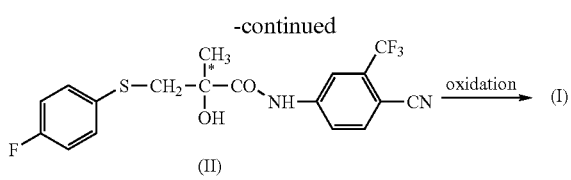

The starting material, the 2,3-dihydroxy-2-methyl-propionic acid of formula (VII), was prepared from the commercially available methacrylic acid by oxidation with 40% aqueous hydrogen peroxide in the presence of tungstic acid catalyst.

If the starting material was the racemic 2,3-dihydroxy-2-methyl-propionic acid of formula (VII), then the racemic final product was obtained via racemic intermediates. If one of the optically pure antipode of 2,3-dihydroxy-2-methyl-propionic acid of formula (VII) was used as starting material in the above process. then the intermediates were optically pure compounds and the last oxidation step results in one of the optically pure antipode of N-[4-cyano-3-trifluoromethyl-phenyl]-3-[4-fluorophenyl-sulfonyl]-2-hydroxy-2-methyl-propionamide. Since the further reaction steps of our invention can be carried out under the same reaction conditions for both the racemic both the optically pure enantiomers giving the same yield, we do not mention the optical purity of the chiral intermediates and the products in the following description. (The synthesis of the optically pure enantiomers of 2,3-dihydroxy-2-methyl-propionic acid was described in detail in the experimental part.)

The above given steps of the process according to our invention are described in detail as follows:

The 2,3-dihydroxy-2-methyl-propionic acid of formula (VII) was reacted with thionyl chloride preferably in toluene solution in the presence of pyridine as aromatic amine. After completion of the reaction the obtained 4-chloro-carbonyl-4-methyl-1,3,2-dioxathiolane-2-one of formula (VI) was purified in given case by distillation.

In the next step of the reaction sequence the dioxathiolane derivative of formula (VI) was reacted with 4-cyano-3-trifluoromethyl-aniline in the presence of triethylamine as tertiary base between −40 and 0° C., preferably between −20 and −10° C., then after completion of the reaction the formed amide of formula (V) was isolated. The opening of the dioxathiolane ring was carried out in a mixture of water and a solvent miscible with water, preferably in aqueous tetrahydrofuran, under basic conditions, preferably in the presence of an aqueous alkali metal hydroxide solution.

The N-[4-cyano-3-trifluoromethyl-phenyl]-2,3-dihydroxy-2-methyl-propionamide of formula (IV) obtained in the opening reaction of the dioxathiolane ring was reacted with methanesulfonyl chloride or p-toluenesulfonyl chloride or p-bromo-benzenesulfonyl chloride in a halogenated solvent, preferably in dichloromethane, in the presence of a tertiary amine as base, preferably pyridine, between −10 and +10° C., preferably at 0° C., then after completion of the reaction the obtained sulfonyl ester derivative of formula (III)—wherein the meaning of R was methyl, p-tolyl or 4-bromophenyl group—was isolated.

The obtained sulfonyl ester derivative of formula (III)—using the advantage, that the sulfonyl group was a good leaving group—was reacted with 4-fluorothiophenol in an inert atmosphere in isopropanol as solvent in the presence of an inorganic base, i.e. sodium or potassium hydroxide, preferably sodium hydroxide. After completion of the reaction the pH of the reaction mixture was adjusted to neutral, the solution was treated with charcoal, filtered and made basic again to remove the excess of 4-fluorothiophenol. The precipitated crystals were filtered off, washed neutral and dried.

According to our invention the obtained thioether derivative of formula (II) can be oxidized to Bicalutamide by several oxidizing agents. So the thioether derivative of formula (II) can be oxidized with an inorganic peroxy salt, preferably with a combination of potassium hydrogenpersulfate/potassium hydrogensulfate/potassium sulfate known as Oxone®, in a mixture of water and a solvent miscible with water or not miscible with water. If the used solvent was not miscible with water, then a phase transfer catalyst was used to increase the speed of the reaction. The used solvent miscible with water was preferably a $C_1$ to $C_4$ alkanol and the solvent not miscible with water was an ester or a halogenated hydrocarbon. As alkanol preferably methanol was used, while as ester type solvent preferably ethyl acetate was used. As halogenated solvent dichloromethane can be used in the oxidation reaction.

As oxidizing agent concentrated aqueous hydrogen peroxide solution can also be used. In this case the thioether derivative of formula (II) was dissolved in a C1–C4 aliphatic carboxylic acid and the aqueous hydrogen peroxide solution was added to this. The aliphatic carboxylic acid was preferably formic acid or acetic acid. The thioether derivative of formula (II) can also be oxidized under aqueous basic conditions with hydrogen peroxide. In this case a solvent miscible with water can also be used. An aqueous solution of an alkali metal carbonate was preferably used as basic medium and acetonitrile or $C_1$ to $C_4$ alkanol, preferably methanol was used as solvent miscible with water.

According to our invention the oxidation with aqueous hydrogen peroxide solution can also be carried out in a solvent not miscible with water in the presence of a phase transfer catalyst and a salt of a metal belonging to the vanadium or chromium group. In this case a halogenated solvent, preferably dichloromethane was used as solvent not miscible with water and sodium tungstate or ammonium molybdate was used as a salt of a metal belonging to the vanadium or chromium group. In this case a phase transfer catalyst was used to increase the speed of the reaction.

A tetraalkyl ammonium salt was preferably used as phase transfer catalyst in the oxidation step of our invention, not limiting examples: tetrabutylammonium chloride and hydrogensulfate or cetyltrimethylammonium chloride and hydrogensulfate.

In the above oxidation steps an adduct of hydrogen peroxide and urea, dimethyl dioxirane, potassium hydrogenpersulfate or hydrogen peroxide/ammonium molybdate can also be used instead of aqueous hydrogen peroxide.

Several of the intermediates of the invention were new compounds such as the (+)-2,3-dihydroxy-2-methyl-propionic acid sodium salt and the (−)-2,3-dihydroxy-2-methyl-propionic acid sodium salt of formula (VII)

the (±)-4-chloro-carbonyl-4-methyl-1,3,2-dioxathiolane-2-one and the optically pure(+)-4-chloro-carbonyl-4-methyl-1,3,2-dioxathiolane-2-one and (−)-4-chloro-carbonyl-4-methyl-1,3,2-dioxathiolane-2-one of formula (VI)

the (±)-N-[4-cyano-3-trifluoromethyl-phenyl]-2,3-dihydroxy-2-methyl-propionamide and the optically pure (+)-N-[4-cyano-3-trifluoromethyl-phenyl]-2,3-dihydroxy-2-methyl-propionamide and (−)-N-[4-cyano-3-trifluoromethyl-phenyl]-2,3-dihydroxy-2-methyl-propionamide of formula (IV)

(±)-N-[4-cyano-3-trifluoromethyl-phenyl]-2-hydroxy-2-methanesulfonyl-oxy-2-methyl-propionamide and the optically pure (+)-N-[4-cyano-3-trifluoromethyl-phenyl]-2-hydroxy-2-methanesulfonyloxy-2-methyl-propionamide and (−)-N-[4-cyano-3-trifluoromethyl-phenyl]-2-hydroxy-2-methane-sulfonyloxy-2-methyl-propionamide, the (±)-N-[4-cyano-3-trifluoromethyl-phenyl]-2-hydroxy-3-[4-methylphenyl-sulfonyloxy]-2-methyl-propionamide and the optically pure (+)-N-[4-cyano-3-trifluoromethyl-phenyl]-2-hydroxy-3-[4-methylphenyl-sulfonyloxy]-2-methyl-propionamide and (−)-N-[4-cyano-3-trifluoromethyl-phenyl]-2-hydroxy-3-[4-methyl-phenyl-sulfonyloxy]-2-methyl-propionamide, the (±)-N-[4-cyano-3-trifluoromethyl-phenyl]-2-hydroxy-3-[4-bromophenyl-sulfonyloxy]-2-methyl-propionamide and the optically pure (+)-N-[4-cyano-3-trifluoromethyl-phenyl]-2-hydroxy-3-[4-bromophenyl-sulfonyl-oxy]-2-methyl-propionamide and (−)-N-[4-cyano-3-trifluoromethyl-phenyl]-2-hydroxy-3[4-bromophenyl-sulfonyloxy]-2-methyl-propionamide of formula (III).

The starting material of the last step of the synthesis and the final product were known, but our invention describes a new process for the synthesis of the latter—and for the synthesis of the new compounds as well—as mentioned above.

The process according to our invention not only solves the synthesis of the final product partly via new compounds, but fulfils the economical and environmental protective requirements of an industrial synthesis as well. The advantages of our process were the following:

1) The starting material of the synthesis was easily available and cheap.
2) The starting material makes possible the synthesis of such intermediates, which were suitable for the synthesis of the pure enantiomers of the final product.
3) The reaction conditions of the oxidation steps were safe and can be carried out without environmental pollution.
4) The use of inflammable sodium hydride can be avoided during the course of the synthesis.
5) our process does not use reagents, which were especially harmful for health, i.e. potassium cyanide in acidic medium.
6) The industrial realization of our process does not need special equipment—in contrast to the known procedure (i.e. acid and pressure resistant autoclave for the hydrolysis of the cyanohydrine in concentrated hydrochloric acid at 110° C.).
7) The products were obtained pure enough, so their further purification can be solved with simple purification methods, the chromatography can be avoided.
8) The procedures known from the literature describe the synthesis of optically active Bicalutamide either by resolution of the racemic compound of formula (II), which was the last intermediate of the synthesis, and oxidation of the resolved intermediate or by asymmetric synthesis from S-(−)-methacryloyl-proline, which was not easily available and expensive starting material. In the previous case half of the synthesized compound of formula (II)—the unwanted enantiomer was lost, while in the second case the starting material of the synthesis was hardly accessible.

The process according to our invention was illustrated in detail by the following not limiting examples.

EXAMPLE 1

Racemic and optically pure 2,3-dihydroxy-2-methyl-propionic acid a) The synthesis of racemic 2,3-dihydroxy-2-methyl-propionic acid:

A mixture of 76.0 g of water, 51.0 g of 40% aqueous hydrogen peroxide and 1.0 g of tungstic acid was stirred at 55–60° C. for 1 h, then the so obtained pertungstic acid—hydrogen peroxide reagent was cooled to 30–35° C. A solution of 33.9 ml (0.4 mol) of methacrylic acid and 0.66 g (6.0 mmol) of hydroquinone in 70 g of water was added to the pertungstic acid—hydrogen peroxide reagent. After the addition the reaction mixture was stirred at 60° C. for 7 h, then it was extracted twice with 50 ml of ethyl acetate. A suspension of 0.1 g of palladium on charcoal catalyst and 5 g of water was added to the water phase and the mixture was stirred at 70–72° C. for 1 h. The catalyst was filtered off, the filtrate was concentrated in vacuum and the residue was recrystallized from acetonitrile to yield 30.3–31.2 g (63.1–65%) of the racemic title compound.

b) The synthesis of R-(−)-2,3-dihydroxy-2-methyl-propionic acid:

12.01 g (0.1 mol) of racemic 2,3-dihydroxy-2-methyl-propionic acid was refluxed in 60 ml of acetone until the solid material was dissolved, then the heating was stopped and 14.27 g (0.05 mol) of (+)-dehydro-abiethylamine in 14 ml of acetone was added. After the addition crystal seeds of pure R-(−)-2,3-dihydroxy-2-methyl-propionic acid -(+)-dehydro-abiethylamine salt was added. The mixture was cooled to −5° C. and stirred at this temperature for 30 min. The precipitated crystals were filtered off, washed with 12 ml of acetone cooled to −5° C. and dried to yield 15.1 g of crude R-(−)-2,3-dihydroxy-2-methyl -propionic acid -(+)-dehydro-abiethylamine salt. Mp: 170–180° C. (The mother liquor obtained in the resolution was concentrated in vacuum and the obtained 11.3 g of residue was used for the resolution of the S-(+)-antipode.)

The obtained 15 g of crude R-(−)-2,3-dihydroxy-2-methyl-propionic acid -(+)-dehydro-abiethylamine salt was dissolved in dry ethanol, the solution was cooled to −5° C. and stirred at this temperature for 30 min. the precipitated crystals were filtered off washed with 8 ml of dry ethanol cooled to −5° C. and dried to yield 6.6 g of pure R-(−)-2,3-dihydroxy-2-methyl -propionic acid -(+)-dehydro-abiethylamine salt as white, crystalline compound. Mp: 196–197° C. [α]D =+22.6 (c=1, ethanol). [a]$_{365}$=+75.9° (c=1, ethanol). (The mother liquor obtained in the recrystallization was concentrated in vacuum and the obtained 8.4 g of residue was used for the resolution of the S-(+)-antipode.)

6.5 g of R-(−)-2,3-dihydroxy-2-methyl-propionic acid —(+)-dehydro-abiethylamine salt was suspended in 13 ml of water and a calculated amount of 10% aqueous sodium hydroxide solution was added. Then 20 ml of chloroform was added to the reaction mixture vigorously stirred then let them separate. After the separation of the phases the pH of the water phase was checked and in given case adjusted to 12. Then the phases were separated, the water phase was extracted three times with 20 ml of chloroform, then concentrated in vacuum to yield 2.2 g of optically pure R-(−)-2,3-dihydroxy-2-methyl-propionic acid sodium salt as white, crystalline powder. Hp: 178–179° C. [α]D =−3.6° (c=1, water). [α]$_{365}$=−13.1° (c=1, water).

5 g of R-(−)-2,3-dihydroxy-2-methyl-propionic acid sodium salt was dissolved in 5 ml of water and 15 g of 10% aqueous hydrochloric acid was added. The so obtained aqueous solution was concentrated under diminished pressure and twice 10 ml of acetonitrile was distilled off from the residue. The residue was dissolved in 25 ml of acetonitrile, the precipitated sodium chloride was filtered off and washed twice with 5 ml of acetonitrile. The combined acetonitrile phase was concentrated under diminished pressure to yield 4.22 g of R-(−)-2,3-dihydroxy-2-methyl-propionic acid. Mp: 68–70° C. [α]D=−2.6 (c=1, water). [α]$_{365}$=−6.1 (c=1. water).

The residues collected for the resolution of the S-(+)-antipode were combined, the so obtained 19.7 g material was dissolved in 40 ml of ion-exchanged water 20 ml of chloroform was added and the pH of the stirred mixture was adjusted to 12 by adding 10% aqueous sodium hydroxide solution. After separation of the phases the water phase was extracted three times with 20 ml of chloroform. This chloroform solution was combined with chloroform solutions obtained during the preparation of R-(−)-2,3-dihydroxy-2-methyl-propionic acid sodium salt, dried over sodium sulfate and concentrated to yield 13.85 g of S-(+)-2,3-dihydroxy-2-methyl-propionic acid.

The water phase obtained above was acidified with 3 M aqueous hydrochloric acid to pH =2 and concentrated in vacuum. 50 ml of acetone was added to the residue and the 2,3-dihydroxy-2-methyl-propionic acid was dissolved from beside the sodium chloride. The acetone solution was concentrated, 8 ml of acetonitrile and subsequently seeds of 2,3-dihydroxy-2-methyl-propionic acid were added, the mixture was cooled to 0° C. and stirred at this temperature for 30 min. The precipitated 2,3-dihydroxy-2-methyl-propionic acid was filtered off, washed twice with 4 ml of acetonitrile cooled to 0° C. and dried to yield 8.15 g of racemic 2,3-dihydroxy-2-methyl-propionic acid, which has the S-(+)-antipode as impurity. Mp: 95–100° C.

Concentration of the acetonitrile solution yields further 1.65 g of optically pure S-(+)-2,3-dihydroxy-2-methyl-propionic acid.

EXAMPLE 2

4-Chloro-carbonyl-4-methyl-1,3,2-dioxathiolane-2-one

A mixture of 75 g (0.624 mol) of 2,3-dihydroxy-2-methyl-propionic acid. 2000 ml of toluene and 1.5 ml of pyridine was cooled to 10° C. and 112.5 ml (1.524 mol) of thionyl chloride was added. After the addition the mixture was refluxed for 4 h, then concentrated under diminished pressure and the residue was distilled in vacuum. The boiling point of the title compound was 62° C. at 6.5 mbar. The optically pure isomers were synthesized analogously.

| Title Compound | Yield [g] | Yield [%] | Boiling point at 6.5 mbar [° C.] |
|---|---|---|---|
| racemate | 90.0 | 78.0 | 62 |
| R-(−) | 86.5 | 75.0 | 62 |
| S-(+) | 83.1 | 72.0 | 62 |

EXAMPLE 3

N-[4-cyano-3-trifluoromethyl-phenyl]-2,3-dihydroxy-2-methyl-propionamide

To a solution of 44 g (0.236 mol) of 4-cyano-3-trifluoromethyl-aniline in 880 ml of dichloromethane 90 ml of triethylamine was added and the reaction mixture was cooled to −15° C. 64 ml (0.49 mol) of 4-chloro-carbonyl-4-methyl-1,3,2-dioxathiolane-2-one was added dropwise at this temperature. The reaction mixture was stirred at 0° C. for 3 h, then extracted with 500 ml of 10% hydrochloric acid solution, the organic layer was dried over sodium sulfate and concentrated under diminished pressure. The residue was dissolved in 1 l of tetrahydrofuran and 440 ml of 10% sodium hydroxide solution was added at 10° C. with cooling. The mixture was stirred for 30 min, then the pH was adjusted to 2 by adding 88 ml of concentrated hydrochloric acid and the solution was evaporated to a volume of 100 ml. The residue was dissolved in 260 ml of ethyl acetate, treated with charcoal, filtered and 520 ml of petroleum ether was added to the filtrate. The precipitated crystals were filtered off and dried at 60° C. in vacuum. The compounds below were synthesized analogously, using the same quantity of the starting material:

| Title compound | Yield [g] | Yield [%] | Melting point [° C.] | [α]D$^{22}$ [°] (c = 1, methanol) |
|---|---|---|---|---|
| racemate | 46.64 | 68.5 | 107–108 | — |
| R-(−) | 55.87 | 82.0 | 130–131 | −43.6 |
| S-(+) | 55.87 | 82.0 | 132–133 | +43.2 |

EXAMPLE 4

N-[4-cyano-3-trifluoromethyl-phenyl]-2-hydroxy-3-methanesulfonyloxy-2-methyl-propionamide A solution of 46 g (0.16 mol) of N-[4-cyano-3-trifluoromethyl-phenyl]-2,3-dihydroxy-2-methyl-propionamide in 1 l of dichloromethane and 46 ml (0.57 mol) of dry pyridine was cooled to 0° C. and 46 ml (0.59 mol) of methanesulfonyl chloride was added dropwise. The mixture was stirred at 0° C. for 5 h, then washed three times with 500 ml of saturated aqueous sodium hydrogen carbonate, 500 ml of 10% aqueous hydrochloric acid and 500 ml of brine. The organic layer was dried over sodium sulfate and concentrated in vacuum. The residue was crystallized with 200 ml of petroleum ether, which has a boiling range of 40–70° C.

The following compounds were synthesized analogously using the same quantity of the starting material:

| Title compound | Yield (g) | Yield [%] | Melting point [° C.] | [α]D$^{22}$ [°] (c = 1, methanol) |
|---|---|---|---|---|
| racemate | 49.70 | 85 | 119–120 | — |
| R-(−) | 52.62 | 90 | 106–107 | −43.1 |
| S-(+) | 52.62 | 90 | 118–119 | +43.1 |

EXAMPLE 5

N-[4-cyano-3-trifluoromethyl-phenyl]-2-hydroxy-3-[4-methylphenyl-sulfonyloxy]-2-methyl-propionamide A solution of 5 g (17.35 mol) of N-[4-cyano-3-trifluoromethyl-phenyl]-2,3-dihydroxy-2-methyl-propionamide in 50 ml of dry pyridine was cooled to 0° C. and 10 g (52.45 mmol) of p-toluenesulfonyl chloride was added in small portions. The mixture was stirred at 0° C. for 5 h, then diluted with 200 ml of dichloromethane, washed three times with 50 ml of saturated aqueous sodium hydrogen carbonate, twice with 50 ml of 10% aqueous hydrochloric acid and 50 ml of brine. The organic layer was dried over sodium sulfate and concentrated in vacuum. The residue was crystallized from a 1:5 mixture of ethyl acetate/petroleum ether, which has a boiling range of 40–70° C.

The following compounds were synthesized analogously using the same quantity of the starting material:

| Title compound | Yield (g) | Yield [%] | Melting point [° C.] | $[\alpha]D^{22}$ [°] (c = 1, methanol) |
|---|---|---|---|---|
| racemate | 6.80 | 85 | 140–141 | — |
| R-(−) | 6.52 | 82 | 125–126 | −42.9 |
| S-(+) | 6.52 | 82 | 125–127 | +42.6 |

EXAMPLE 6

N-[4-cyano-3-trifluoromethyl-phenyl]-2-hydroxy-3-[4-bromophenyl-sulfonyloxy]-2-methyl-propionamide A solution of 5 g (17.35 mmol) of N-[4-cyano-3-trifluoromethyl-phenyl]-2,3-dihydroxy-2-methyl-propionamide in 50 ml of dry pyridine was cooled to 0° C. and 8.86 g (34.70 mmol) of 4-bromo-benzenesulfonyl chloride was added in small portions. The mixture was stirred at 0° C. for 5 h, then diluted with 200 ml of dichloromethane, washed three times with 50 ml of saturated aqueous sodium hydrogencarbonate, twice with 50 ml of 10% aqueous hydrochloric acid and 50 ml of brine. The organic layer was dried over sodium sulfate and concentrated in vacuum. The residue was crystallized from a 1:5 mixture of ethyl acetate/petroleum ether, which has a boiling range of 40–70° C.

The following compounds were synthesized analogously using the same quantity of the starting material:

| Title compound | Yield (g) | Yield [%] | Melting point [° C.] | $[\alpha]D^{22}$ [°] (c = 1, methanol) |
|---|---|---|---|---|
| racemate | 6.60 | 75 | 135–137 | — |
| R-(−) | 6.86 | 78 | 122–124 | −44.4 |
| S-(+) | 6.60 | 75 | 123–124 | +44.2 |

EXAMPLE 7

N-[4-cyano-3-trifluoromethyl-phenyl]-3-[4-fluorophenyl-thio]-2-hydroxy-2-methyl-propionamide Under nitrogen, to a solution of 25.6 g (0.20 mol) of 4-fluorthiophenol in 500 ml of isopropanol 8.4 g (0.20 mol) of sodium hydroxide in 400 ml of water was added. The mixture was stirred at 25° C. for 2 h, then 58.6 g (16 mmol) of N-[4-cyano-3-trifluoromethyl-phenyl]-2-hydroxy-3-(methanesulfonyloxy)-2-methyl-propionamide in 500 ml of isopropanol was added. Then the mixture was stirred at 25° C. for 5 h, then the pH was adjusted to neutral with concentrated hydrochloric acid and treated with charcoal at reflux temperature. Most of the isopropanol was evaporated in vacuum and 250 ml of 2% aqueous sodium hydroxide solution was added to the residue under vigorous stirring, then the crystalline mixture was left for 1 h, then filtered and washed with water. The dried crystals were recrystallized from a 1:4 mixture of ethyl acetate/petroleum ether, which has a boiling range of 40–70° C.

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 52.88 | 83 | 116–118 | — |
| R-(−) | 54.80 | 86 | 97–98 | −2.80 |
| S-(+) | 52.88 | 83 | 96–97 | +2.68 |

EXAMPLE 8

N-[4-cyano-3-trifluoromethyl-phenyl]-3-[4-fluorophenyl-sulfonyl]-2-hydroxy-2-methyl-propionamide A solution of 52 g (0.13 mol) of N-[4-cyano-3-trifluoromethyl-phenyl]-3-[4-fluorophenylthio]-2-hydroxy-2-methyl-propionamide in 520 ml of acetic acid was cooled to 10° C. and 156 ml of 30% aqueous hydrogen peroxide solution was added. The reaction mixture was stirred overnight, then poured into 3 l of saturated aqueous sodium hydrogencarbonate and extracted three times with 500 ml of dichloromethane, then the combined organic layers were washed with 500 ml of brine, dried over sodium sulfate and concentrated under diminished pressure. The residue was dissolved in 500 ml of ethyl acetate, cooled to +5° C. and 2000 ml of petroleum ether, which has a boiling range of 40–70° C., was added. The precipitated crystals were filtered off, washed with 40 ml of petroleum ether cooled to 0° C. and dried at 60° C. in vacuum.

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 47.25 | 84.15 | 191–193 | — |
| R-(−) | 47.66 | 84.88 | 181–182 | −80.04 |
| S-(+) | 46.14 | 82.17 | 180–181 | +79.7 |

EXAMPLE 9

N-[4-cyano-3-trifluoromethyl-phenyl]-3-[4-fluorophenyl-sulfonyl]-2-hydroxy-2-methyl-propionamide The reaction was carried out as described in Example 8, with the difference that 520 ml of formic acid was used instead of acetic acid.

The following compounds were synthesized analogously using the same quantity of the starting material:

| Title compound | Yield [g] | Yield [%] | $[\alpha]D^{22}$ [°] (c = 1, methanol) |
|---|---|---|---|
| racemate | 45.01 | 80.15 | — |
| R-(−) | 46.20 | 82.28 | −80.12 |
| S-(+) | 43.64 | 77.71 | +79.83 |

EXAMPLE 10

N-[4-cyano-3-trifluoromethyl-phenyl]-3-[4-fluorophenyl-sulfonyl]-2-hydroxy-2-methyl-propionamide To a solution of 2 g (2.51 mmol) of N-[4-cyano-3-trifluoromethyl-phenyl]-3-[4-fluorophenyl-thio]-2-hydroxy-2-methyl-propionamide in 10 ml of acetonitrile, 20 ml of methanol and 0.6 ml of water 0.38 g (2.75 mmol) of potassium carbonate was added. The mixture was cooled to 5° C. and 10 ml of 30% aqueous hydrogen peroxide solution was added dropwise. The mixture was stirred at 25° C. overnight, then diluted with 100 ml of water and extracted twice with 100 ml of dichloromethane. The organic layer was washed with 50 ml of brine, dried over sodium sulfate and concentrated under diminished pressure. The residue was recrystallized from a 1:4 mixture of ethyl acetate/petroleum ether, which has a boiling range of 40–70° C. The yield was 1.53 g (70.83%).

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 1.53 | 70–83 | 191–193 | — |
| R-(−) | 1.59 | 73.61 | 181–182 | −80.20 |
| S-(+) | 1.46 | 67.59 | 179–180 | +79.92 |

EXAMPLE 11

N-[4-cyano-3-trifluoromethyl-phenyl]-3-[4-fluorophenyl-sulfonyl]-2-hydroxy-2-methyl-propionamide To a solution of 2 g (2.51 mmol) of N-[4-cyano-3-trifluoromethyl-phenyl]-3-[4-fluorophenyl-thio]-2-hydroxy-2-methyl-propionamide in 20 ml of dichloromethane 5 mg of sodium tungstate and 5 mg of tetrabutylammonium hydrogensulfate phase transfer catalyst were added. 8 ml of 30% aqueous hydrogen peroxide solution was added dropwise to the mixture at room temperature and it was stirred for 8 h at this temperature. The phases were separated, the organic phase was washed twice with 20 ml of 10% aqueous sodium thiosulfate solution, then with brine, dried over sodium sulfate and concentrated under diminished pressure. The residue was recrystallized from a 1:4 mixture of ethyl acetate/petroleum ether, which has a boiling range of 40–70° C.

The same quantity of tetrabutylammonium chloride or cetyltrimethyl-ammonium chloride can also be used resulting in the same yield. The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 1.68 | 77.80 | 191–193 | — |
| R-(−) | 1.66 | 76.85 | 181–182 | −80.5 |
| S-(+) | 1.63 | 75.46 | 180–181 | +79.98 |

EXAMPLE 12

N-[4-cyano-3-trifluoromethyl-phenyl]-3-[4-fluorophenyl-sulfonyl]-2-hydroxy-2-methyl-propionamide To a solution of 40 g (0.1 mol) of N-[4-cyano-3-trifluoromethyl-phenyl]-3-[4-fluorophenyl-thio]-2-hydroxy-2-methyl-propionamide in 600 ml of methanol and 400 ml of water 100 g (0.16 mol) of Oxone® oxidizing agent [2KHSO$_5$KHSO$_4$K$_2$SO$_4$ salt] was added. The reaction mixture was stirred at 25° C. for 6 h, then the methanol was distilled off under diminished pressure and the residue was extracted twice with 500 ml of dichloromethane. The organic layer was washed twice with 400 ml of 10% aqueous sodium thiosulfate solution, then with brine, dried over sodium sulfate and concentrated under diminished pressure. The residue was recrystallized from a 1:4 mixture of ethyl acetate/petroleum ether, which has a boiling range of 40–70° C.

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 36.00 | 83.33 | 191–193 | — |
| R-(−) | 37.12 | 85.93 | 181–182 | −80.15 |
| S-(+) | 37.01 | 85.67 | 180–181 | +79.96 |

EXAMPLE 13

N-[4-cyano-3-trifluoromethyl-phenyl]-3-[4-fluorophenyl-sulfonyl]-2-hydroxy-2-methyl-propionamide The reaction was carried as described in Example 12, with the difference that 600 ml of dichloromethane was used instead of 600 ml of methanol and 0.5 g of tetrabutylammonium hydrogensulfate was used as phase transfer catalyst. The N-[4-cyano-3-trifluoromethyl-phenyl]-3-[4-fluorophenyl-sulfonyl]-2-hydroxy-2-methyl-propionamide was isolated from the dichloromethane solution as described in Example 12.

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 34.12 | 78.98 | 191–193 | — |
| R-(−) | 34.55 | 79.97 | 181–182 | −80.10 |
| S-(+) | 33.71 | 78.03 | 180–181 | +79.89 |

EXAMPLE 14

N-[4-cyano-3-trifluoromethyl-phenyl]-3-[4-fluorophenyl-sulfonyl]-2-hydroxy-2-methyl-propionamide The reaction was carried as described in Example 12, with the difference that 600 ml of ethyl acetate was used instead of 600 ml of methanol and 0.5 g of tetrabutylammonium hydrogensulfate was used as phase transfer catalyst. The N-[4-cyano-3-trifluoromethyl-phenyl]-3-[4-fluorophenyl-sulfonyl]-2-hydroxy-2-methyl-propionamide was isolated from the ethyl acetate solution as described in Example 12.

The following compounds were synthesized analogously using the same quantity of the starting material:

| Title compound | Yield [g] | Yield [%] | Melting point [° C.] | $[\alpha]D^{22}$ [°] (c = 1, methanol) |
|---|---|---|---|---|
| racemate | 36.77 | 85.12 | 191–193 | — |
| R-(−) | 37.11 | 85.90 | 181–182 | −80.16 |
| S-(+) | 36.16 | 83.71 | 180–181 | +79.91 |

What is claimed is:

1. A process for the synthesis of racemic or optically pure R-(−)- and S-(+)-N-[4-cyano-3-trifluoro methyl-phenyl]-3-[4-fluorophenyl-sulfonyl]-2-hydroxy-2-methylpropionamide of formula (I), (Ia) and (Ib), respectively,

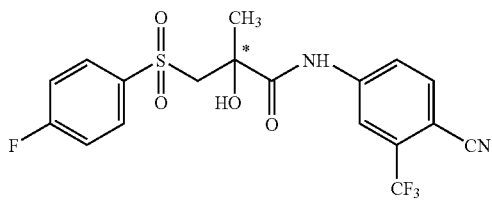
(I)

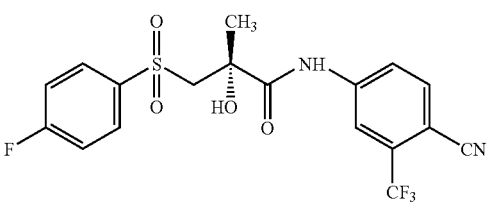
(Ia)

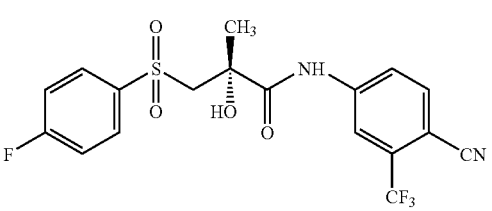
(Ib)

which comprises the steps of:

(a) reacting racemic or optically pure 2,3-dihydroxy-2-methyl-propionic acid of formula (VII)

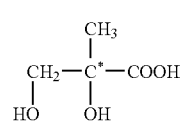
(VII)

with thionyl chloride in a halogenated hydrocarbon or in an aromatic solvent in the presence of an aromatic amine as base to obtain a compound of the Formula (VI)

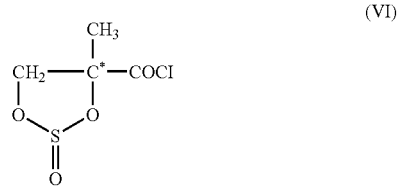
(VI)

(b) reacting the obtained racemic or optically pure 4-chloro-carbonyl-4-methyl-1,3,2-dioxathiolane-2-one of the Formula (VI) with 4-cyano-3-trifluoromethyl-aniline in an inert solvent in the presence of a tertiary amine as base between −40 and 0° C. to obtain racemic or optically pure 4-{[4-cyano-3-(trifluoromethyl)-anilino]-carbonyl}-4-methyl-1,3,2-dioxathiolane-2-one of formula (V)

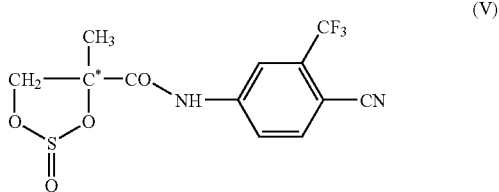
(V)

(c) hydrolyzing the obtained racemic or optically pure 4-{[4-cyano-3-(trifluoromethyl)-anilino]-carbonyl}-4-methyl-1,3,2-dioxathiolane-2-one of formula (V) under aqueous basic conditions to obtain racemic or optically pure N[4-cyano-3-(trifluoromethyl)-phenyl]-2,3-dihydroxy-2-methyl-propionamide of formula (IV)

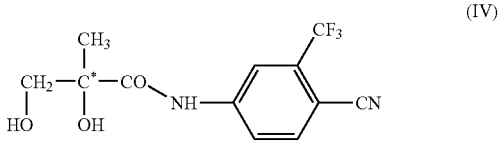
(IV)

(d) sulfonylating the formed racemic or optically pure N-[4-cyano-3-(trifluoromethyl)-phenyl]-2,3-dihydroxy-2-methyl-propionamide of formula (IV) with a sulfonyl halogenide of formula

R—SO$_2$—X wherein the meaning of R is methyl, p-tolyl or p-bromo-phenyl and X is a halogen atom—in a halogenated hydrocarbon as solvent in the presence of a tertiary amine as base to obtain a compound of the Formula (III)

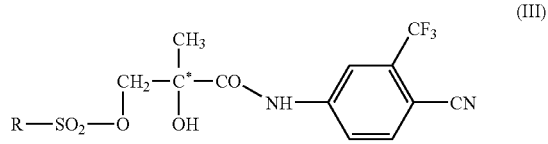
(III)

(e) reacting the obtained racemic or optically pure compound of the Formula (III) wherein R is methyl, p-tolyl or p-bromo-phenyl with 4-fluorothiophenol in the presence of a base, to obtain a racmic or optically active thioether compound of the Formula (II)

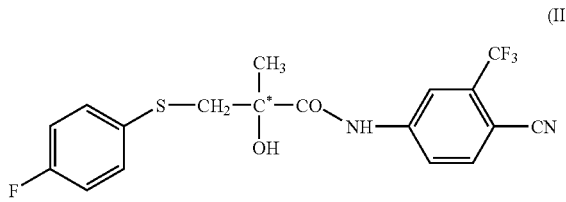

and
(f) finally oxidizing the obtained racemic or optically pure thioether of the Formula (II) with
(I) an inorganic peroxy salt in a mixture of water and a solvent miscible or not miscible with water, in the latter case in the presence of a phase transfer catalyst, or
(ii) aqueous hydrogen peroxide
A) in a $C_1$–$C_4$ aliphatic carboxylic acid, or
B) under aqueous basic conditions, in the presence of an organic solvent miscible with water, or
C) in an organic solvent not miscible with water in the presence of a phase transfer catalyst and a salt of a metal belonging to the vanadium or chromium group to obtain the compound of the Formula (I), (Ia) or (Ib).

2. The process defined in claim 1, wherein according to step (a) the reaction of the racemic or optically pure 2,3-dihydroxy-2-methyl-propionic acid with thionyl chloride is carried out in dichloromethane, chloroform or 1,2-dichloroethane as halogenated hydrocarbon, or in benzene, toluene or xylene as aromatic solvent in the presence of pyridine as aromatic base.

3. The process defined in claim 1, wherein according to step (b) the reaction of the racemic or optically pure 4-chlorocarbonyl-4-methyl-1,3,2-dioxathiolane-2-one of formula (VI) with 4-cyano-3-trifluoromethyl-aniline is carried out in the presence of triethylamine as tertiary amine base.

4. The process defined in claim 3, wherein a halogenated or an aromatic hydrocarbon or an ether type solvent is used as an inert solvent.

5. The process defined in claim 3, wherein the reaction is carried out between –15 and 0° C.

6. The process defined in claim 1, wherein according to step (c) the hydrolysis of the racemic or optically pure 4-{[4-cyano-3-(trifluoromethyl)-anilino]-carbonyl}-4-methyl-1,3,2-dioxathiolane-2-one of formula (V) is carried out in an aqueous medium containing an alkali metal hydroxide.

7. The process defined in claim 1, wherein according to step (d) sulfonylating the racemic or optically pure [4-cyano-3-(trifluoromethyl-phenyl]-2,3-dihydroxy-2-methyl-propionamide of formula (IV) is carried out in dichloromethane as the halogenated hydrocarbon solvent in the presence of pyridine as the tertiary amine base.

8. The process defined in claim 1 wherein according to step (e) the racemic or optically pure compound of the Formula (III) is reacted with 4-fluorothiophenol in the presence of an inorganic base.

9. The process defined in claim 1, wherein according to step (f), part (I) the racemic or optically pure thioether of the Formula (II) is oxidized with a mixture of $2KHSO_5KHSO_4K_2SO_4$ (OxoneO) as inorganic peroxy salt.

10. The process defined in claim 9, wherein the oxidation is carried out in a mixture of methanol and water.

11. The process defined in claim 9, wherein the oxidation is carried out in a mixture of dichloromethane and water in the presence of a phase transfer catalyst.

12. The process defined in claim 9, wherein the oxidation is carried out in a mixture of ethyl acetate and water in the presence of a phase transfer catalyst.

13. The process defined in claim 1, wherein according to step (f), part (ii)(A) the oxidation of the racemic or optically pure thioether of the Formula (II) is carried out in formic acid or acetic acid as $C_1$–$C_4$ aliphatic carboxylic acid in the presence of aqueous hydrogen peroxide.

14. The process defined in claim 1, wherein according to step (f), part (ii)(B) the oxidation of the racemic or optically pure thioether of the Formula (II) is carried out in aqueous alkali metal carbonate solution in the presence of acetonitrile and/or a $C_1$–$C_4$ alkanol as the organic solvent miscible with water in the presence of aqueous hydrogen peroxide.

15. The process defined in claim 1, wherein according to step (f), part (ii)(C) the oxidation of the racemic or optically pure thioether of the Formula (II) is carried out in a halogenated hydrocarbon as the organic solvent not miscible with water in the presence of a quaternary ammonium salt as phase transfer catalyst and sodium tungstate with aqueous hydrogen peroxide.

16. The process defined in claim 11 wherein tetrabutyl-ammonium hydrogensulfate, cetyltrimetylammonium chloride or tetrabutyl-ammonium chloride is used as phase transfer catalyst.

17. The process defined in claim 12 wherein tetrabutyl-ammonium hydrogensulfate, cetyltrimetylammonium chloride or tetrabutyl-ammonium chloride is used as phase transfer catalyst.

18. The process defined in claim 15 wherein tetrabutyl-ammonium hydrogensulfate, cetyltrimetylammonium chloride or tetrabutyl-ammonium chloride is used as phase transfer catalyst.

* * * * *